US005567301A

United States Patent [19]
Stetter et al.

[11] Patent Number: 5,567,301
[45] Date of Patent: Oct. 22, 1996

[54] ANTIBODY COVALENTLY BOUND FILM IMMUNOBIOSENSOR

[75] Inventors: Joseph R. Stetter, Naperville; Peter J. Hesketh, Chicago; Steven M. Gendel, Naperville; G. Jordan Maclay, Maywood, all of Ill.

[73] Assignees: Illinois Institute of Technology, Chicago, Ill.; United States of America, Washington, D.C.

[21] Appl. No.: 396,229

[22] Filed: Mar. 1, 1995

[51] Int. Cl.$^6$ .................................................. G01N 27/26
[52] U.S. Cl. .................. 205/777.5; 204/403; 204/415; 435/4; 435/7.1; 435/7.93; 435/817; 435/287.2
[58] Field of Search ............................ 204/403, 415, 204/153.12; 435/817, 288, 291, 4, 7.1, 7.93

[56] References Cited

U.S. PATENT DOCUMENTS

| | | | |
|---|---|---|---|
| 4,822,566 | 4/1989 | Newman | 422/68 |
| 5,053,225 | 10/1991 | Miyasaka et al. | 424/85.8 |
| 5,074,977 | 12/1991 | Cheung et al. | 204/153.1 |
| 5,077,210 | 12/1991 | Eigler et al. | 435/176 |
| 5,137,827 | 8/1992 | Mroczkowski et al. | 435/288 |
| 5,171,779 | 12/1992 | Hsu et al. | 525/54.1 |
| 5,200,051 | 4/1993 | Cozzette et al. | 204/403 |
| 5,242,828 | 9/1993 | Bergström et al. | 435/291 |
| 5,269,903 | 12/1993 | Ikariyama et al. | 204/403 |

OTHER PUBLICATIONS

Sibbald, A. J., *J. Mole. Elec.* 1986, 2, 51–83.
Buch, R. M. et al., *Analytic Chemistry*, 1989, 61, 533A.
Thompson, M. et al., *Analytic Chemistry*, 1991, 63, 393A.
Sutherland, R. M. et al., *Clinical Chemistry*, Winston-Salem, N.C. 1984, 30,9 1533–1538.
Aizawa et al., Proc. Int. Meet. Chem. Sens. 2nd, 1986, 6–30, 622–625.
Bataillard, P. et al., *Analytical Chemistry*, 1988, 60, 2374–2379.
Newman et al., W.D. Proc. Int. Meet. Chem. Sens., 2nd, 1986, 6–23, 596–598.
Hesketh, P. J. et al., *Sensors and Actuators B*, 1993, 13–14, 749–751.
Kasapbasiolgu, B., M.S. Thesis, University of Illinois, Chicago, 1992, 1–63.
Bhatia et al., *Analytic Biochemistry*, 1989, 178, 408–413.
Darnell, James, et al., *Scientific American Books*, "Molecular Cell Biology" 1986, pp. 78–81, 1081–1123.
Chantler, S., et al., *Immunology for the 80s*, "Current Status of Specific IgM Antibody Assays", 417–430.
Avrameas, S., et al., *Proceedings of the Second International Symposium on Immunoenzymatic Techniques*, "Immunoenzymatic Techniques", 127–175, 1983.

*Primary Examiner*—Bruce F. Bell
*Attorney, Agent, or Firm*—Speckman, Pauley & Fejer

[57] ABSTRACT

A biosensor comprising a substrate material, at least one antibody covalently immobilized on the substrate material, and a pair of metal contact electrodes for measuring the impedance of the biosensor. A process for producing a biosensor in accordance with this invention as well as a process for utilizing the biosensor are also disclosed.

25 Claims, 6 Drawing Sheets

ANTIBODY COVALENTLY BOUND FILM IMMUNOBIOSENSOR

BACKGROUND OF THE INVENTION

1. Field of the Invention

This invention relates to an immunobiosensor for sensing antigens, a process for producing such an immunobiosensor, and a process for sensing antigens with said immunobiosensor. Immuno-biosensing techniques to measure specific antigen-antibody binding reactions are important in the development of biosensor applications in biotechnology, diagnosis, medicine and food technology.

2. Description of Prior Art

Immunobiosensors are of great interest due to their potential utility as specific and direct detection tools and their simplicity compared to standard immulogic tests, including enzyme linked immunosorbent assays and immunoradiometric assays. See SIBBALD, A. J., *J. Mole. Elec.* 1986, 2, 51–83. Immunobiosensors, like other types of biosensors, utilize a molecular recognition element comprising a transduction system coupled to a receptor. (Buch, R. M. et al., *Analytic Chemistry*, 1989, 61, 533A; Thompson, M. et al., *Analytic Chemistry*, 1991, 63, 393A). The molecular recognition is achieved by sensing a specific antigen-antibody binding reaction at the receptor. The transduction system identifies and responds to the changes in an optical, spectroscopic, chemical, electrochemical, radiochemical, or electrical parameter of the receptor environment due to the specific binding (Sutherland, R. M. et al., *Clinical Chemistry*, Winston-Salem, N.C., 1984, 30, 1533–1538; and Aizawa et al., *Proc. Int. Meet. Chem. Sens. 2nd*, 1986, 6–30, 622–625).

Transduction systems that use capacitive changes for sensing antigen-antibody binding reactions are relatively new. See for example, Bataillard, P. et al., *Analytical Chemistry*, 1988, 60, 2374–2379. Localized capacitances can change with local solution conductivity or as a result of the change in the dielectric constant caused by the antigen-antibody complex formation. Newman et al., *W.D. Proc. Int. Meet. Chem. Sens.*, 2nd, 1986, 6–23, 5966–598 teaches the use of capacitance measurements with photolithographically defined electrodes to develop an immunobiosensor. Bataillard et al. teaches the use of capacitances measurements for the direct detection of antigen-antibody binding. Measurements of a.c. impedances, which includes capacitive changes, however, are not widely employed in immunobiosensors technology (Hesketh, P. J. et al., *Sensors and Actuators B*, 1993, 13–14, 749–751). Similarly, measurements of d.c. impedances are not widely employed in biosensor signal transduction.

The molecular recognition receptor of an immunobiosensor is prepared by immobilizing the biological recognition element, typically antibodies, onto a substrate material. This is a critical step because the antibody activity must remain high after immobilization and binding of antigen to antibody should occur in a manner that reduces interferences (Turner, A.P.F., *Biosensor: Fundamentals and Applications*, Oxford University, 1987, 1–359). U.S. Pat. No. 5,077,210 teaches a method for covalently immobilizing active agents such as proteins on suitable substrates. In accordance with one embodiment, the enzyme acetylcholine esterase is immobilized on a small strip of platinum (Pt) foil. The activity of the immobilized enzyme is measured amperometrically or potentiometricly with the Pt strip as an electrode.

U.S. Pat. No. 5,269,903 teaches a micro-electrode in which enzyme molecules or biologically active substances are immobilized. The micro-bioelectrode is formed by depositing fine particles of a conductive material, such as platinum black, and a biologically active substance on the surface of an electroconductive material, such as Pt. The biologically active substance is then immobilized with a crosslinking agent so as to form an insoluble crosslinked substance in a porous deposition formed by the conductive material.

U.S. Pat. No. 5,074,977 teaches a measuring instrument having a reversibly selective binding protein immobilized upon an insulated-gate region of a field-effect transistor located on a sensor. The '977 patent further discloses immobilizing a binding protein on a silicon dioxide surface of a semi-conducting element. The '977 patent also teaches that the binding protein may also be immobilized by metal such as aluminum, antimony, chrome, gold, platinum or silver to construct an electrode which measures conductance, resistance or potentiometric changes in response to the operation of the binding protein.

U.S. Pat. No. 4,822,566 teaches an electrochemical sensor for determining the concentration of an analyte in a fluid medium. The sensor has two (2) conductors which are coated with a thin electrically insulating passivation layer. Molecules of a binding agent are immobilized on the passivation layer with linking molecules, thereby forming an "open" capacitor. A fluid to be tested for a particular analyte is introduced onto the "open" capacitor. The presence of analyte molecules within the fluid causes a change in the capacitance of the sensor allowing the total concentration of analyte in the test fluid to be determined.

U.S. Pat. No. 5,053,225 teaches a water-insoluble functional organic thin film having a binder with an organic compound and a lipid. The organic thin film is stable and maintains high sensing operability when used with an organic thin film sensor, such as a biosensor.

U.S. Pat. No. 5,242,828 teaches a biosensing surface with a metal film of a free electron metal such as copper, silver, aluminum or gold. A monolayer of an organic molecule X-R-Y is applied to the metal surface. The monolayer binds a desired biospecific molecule or molecular structure which interacts selectively with one or more biomolecules. The molecules may be crosslinked to the monolayer.

U.S. Pat. No. 5,137,827 teaches a method for detecting the occurrence of a binding or complex-forming reaction between specific substances by utilizing the binding reaction to modify an electrical circuit, and then measuring a change in the electrical state of the circuit. A diagnostic element having a layer of antigens coated onto a non-conductive base between a pair of electrical conductors is also disclosed. Antibodies to be tested are bound to fine electrically conductive metallic particles and introduced onto the layer of antigens. Antibodies which react with the layer of antigens bind the electrically conductive particles to the antigen layer and modify the circuit formed by the diagnostic element.

U.S. Pat. No. 5,171,779 teaches a method of immobilizing proteins on a polymeric matrix by plasma activation. The immobilized protein is used in biotransformation or biosensing instruments, as well as for immunoassays.

Finally, U.S. Pat. No. 5,200,051 teaches a method for the microfabrication of electronic devices which have been adapted for the analyses of biologically significant analyte species. Also disclosed is a method for electrochemically detecting a particular analyte species using a substrate/label signal generating pair which produces a change in the concentration of certain electro-active species.

Kasapbasiolgu, B., M.S. Thesis, University of Illinois, Chicago, 1992, 1–63 teaches the immobilization of anti-Staphylococcus Enterotoxin B (SEB) antibodies onto an ultra-thin Pt film through physical adsorption. An impedance decrease was observed during the binding of Staphylococcus Enterotoxin B (SEB) to anti-SEB in phosphate buffered saline (PBS). However, instability of the anti-SEB layer resulted in drift and non-selectivity in the sensor signal. In addition, physically absorbed antibody molecules are likely to leave the substrate surface during sensing. Furthermore, when the antibody is immobilized by entrapment, the antigen-antibody binding reaction is hampered due to both the diffusion barrier experienced by the antigen and escape of antibodies through surface pores (Turner, A. P. F., *Biosensors; Fundamentals and Applications,* Oxford University, 1987, 1–359).

Immobilization through covalent binding using crosslinker molecules is known for building stable layers of antibodies onto substrates surfaces. See, for example, Bhatia et al., *Analytic Biochemistry,* 1989, 178, 408–413. Bataillard, P. et al., *Analytic Chemistry,* 1988, 60, 2374–2379 teaches that anti-α-fetoprotien covalently bound to a silanized glass surface using the crosslinker glutaraldehyde retained its activity. Bhatia et al., *Analytic Biochemistry,* 1989, 178, 408–413 teaches preparation of a receptor for goat-IgG by covalently binding anti-goat-IgG to a glass surface using N-γ-maleimidobutyloxy succinimide ester, GMBS as the crosslinker.

SUMMARY OF THE INVENTION

It is an object of this invention to bind an antibody to a substrate surface for the purpose of determining the presence of a corresponding antigen without loss of activity of the antibody.

It is another object of this invention to provide an immuno-biosensing method that is sensitive, stable, free of interferences, and easy to use.

It is an object of this invention to provide a method and biosensor for detecting the specific binding of SEB to anti-SEB antibodies in PBS solution.

These and other objects of this invention are achieved by a biosensor in accordance with this invention comprising a substrate material, at least one covalently bound antibody immobilized on the substrate material, and impedance detection means for measuring an impedance of the biosensor. More particularly, the biosensor in accordance with one embodiment of this invention comprises an insulator layer passivated on a silicon chip, a discontinuous, preferably ultra-thin, metal film layer deposited on the insulator layer, at least one covalently bound antibody disposed on and/or between the elements of the discontinuous, preferably ultra-thin, metal film layer and insulator layer, and two (2) metal contact electrodes disposed at a distance from one another on the discontinuous ultra-thin metal film layer.

The biosensor in accordance with another embodiment of this invention comprises an insulator layer passivated on a silicon chip, two (2) metal contact electrodes disposed at a distance from one another on the insulator layer, and at least one covalently bound antibody disposed on and/or between the two (2) metal contact electrodes.

To produce a biosensor for measuring antigen-antibody binding reactions in accordance with one embodiment of this invention, the insulator layer is thermally grown on a p-type silicon chip substrate. A discontinuous ultra-thin metal film layer is deposited on the insulator. Two (2) metal contact-electrodes at a distance from one another are secured on the discontinuous ultra-thin metal film layer. And, at least one antibody bioactive layer is covalently immobilized on the discontinuous ultra-thin metal layer.

To measure the antigen-antibody binding reactions in accordance with the process of this invention, a material comprising the desired antigen is contacted with a biosensor comprising a substrate material, covalent antibody immobilization means for immobilizing at least one anti-body corresponding to the desired antigen on the substrate material, and capacitive impedance detection means for measuring the impedance of the biosensor, and the impedance between two (2) metal contact-electrodes of the biosensor is measured.

BRIEF DESCRIPTION OF THE DRAWINGS

These and other objects and features of this invention will be better understood from the following detailed description taken in conjunction with the drawings, wherein.

DESCRIPTION OF PREFERRED EMBODIMENTS

Figure 1:
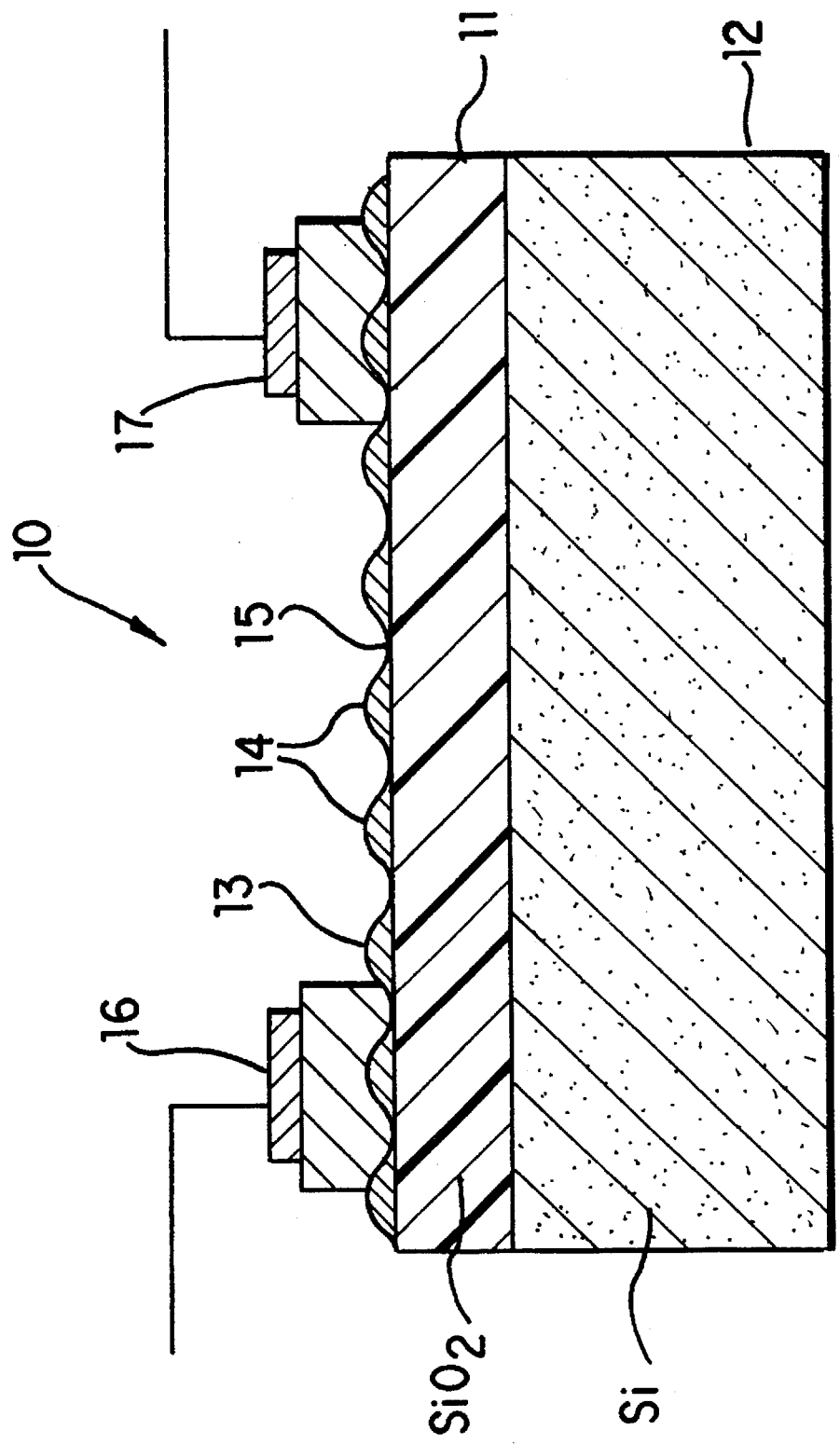
FIG. 1 is a schematic diagram of a biosensor substrate structure for a biosensor in accordance with one embodiment of this invention.

The immunobiosensor of this invention combines a covalent antibody immobilization technique with a simple impedance detection method. The biosensor is fabricated by covalently binding the desired antibodies onto an ultra-thin metal film sputtered onto a silicon chip. Although suitable for use in connection with numerous antibody-antigen pairs, the biosensor discussed herein for illustrative purposes is for detecting the specific binding of SEB to anti-SEB antibodies. The detection and measurement of SEB is carried out in PBS solution. In accordance with this embodiment of the invention, the biosensor is fabricated by covalently binding anti-SEB antibodies onto the surface of a silicon substrate which has been prepared by sputtering of an ultra-thin Pt film onto a 1000 Angstrom, thermally grown oxide film. FIG. 1 shows a schematic diagram of a biosensor substrate structure 10 in accordance with one embodiment of this invention. The biosensor substrate structure 10 comprises an insulator layer 11 passivated on a silicon chip 12. In accordance with a preferred embodiment of this invention, insulator layer 11 is in the form of silicon dioxide. Discontinuous ultra-thin metal film layer 13 is deposited on insulator layer 11, discontinuous ultra-thin metal film layer 13 comprising a plurality of distributed islands 14 with an uncovered portion 15 of the insulator layer 11 disposed between neighboring islands 14. In the biosensor of this invention, the areas between the islands 14, that is uncovered portions 15, are filled with immobilized antibodies. Disposed on discontinuous ultra-thin metal film layer 13 are two (2) metal contact electrodes 16, 17 for use in impedance detection across the sensor.

A biosensor suitable for measuring anti-SEB antibody-SEB antigen activity in accordance with one embodiment of this invention can be constructed as follows. A 100 nm thick layer of silicon dioxide is thermally grown on a p-type, 2-inch diameter silicon chip at 1000° C. in a dry oxygen atmosphere. A discontinuous ultra-thin Pt film is deposited on the silicon dioxide layer by electron beam evaporation at a rate of 0.1 Angstroms per second at $10^{-8}$ torr at room temperature. The Pt film is preferably in the range of about 25 Angstroms thick. The film is composed of regularly distributed Pt islands of radii of about 30–60 Angstroms, leaving an uncovered silicon dioxide surface of about 21–50 Angstroms between neighboring islands.

The distance between neighboring islands varies depending on the specific antigen-antibody reaction being measured. Preferably, the distance between neighboring islands corresponds to a size range of the covalently bound antibody disposed on the discontinuous ultra-thin metal film layer. For anti-SEB antibody—SEB antigen reactions, this size range is about 21–50 Angstroms.

Two (2) Pt contact-electrodes having a thickness of about 100 nm are located on the discontinuous ultra-thin metal layer at a distance of approximately 1.32 mm from each other. This modified silicon chip is then diced into a 4× 4 mm structure and mounted onto the surface of gold plated Kovor 0.9 cm diameter TO-5 header using silver epoxy and cured at 150° C. for about 30 minutes. The two (2) electrodes are connected to the header through gold plated copper wires using silver epoxy and cured at 150° C. for 30 minutes.

The Pt film is then cleaned by immersion in concentrated sulfuric acid for 10 minutes, followed by washing with deionized water and dried under a stream of nitrogen gas. The film is then employed in the sequence of chemical reaction shown herein below to immobilize an anti-SEB layer thereon.

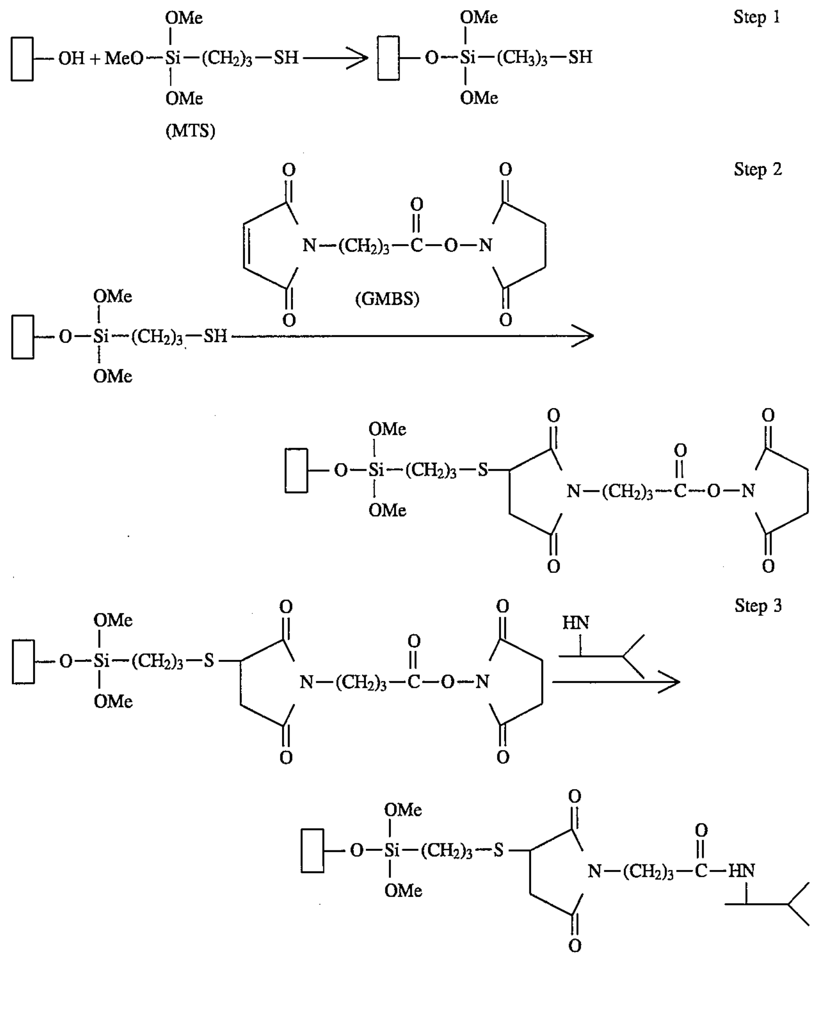

Silanization of the film surface is carried out by treating the surface with a 2% solution of 3-mercaptopropyltrimethoxysilane, MTS in dry toluene under a nitrogen atmosphere for one hour. The film surface is rinsed with dry toluene and dried in a stream of nitrogen gas. This silanized film surface is then reacted with GMBS (2 mM in absolute ethanol) at 4° C. for one hour. After washing with PBS, the chemically modified film surface is reacted with anti-SEB (100 μg/ml anti-SEB in PBS) at 4° C. for twenty-four (24) hours. The biosensor is maintained moist with PBS at 4° C. prior to use.

To enable reuse of the biosensor, the acid cleaning procedure described hereinabove is performed to remove SEB-complexed anti-SEB layers from the Pt film after use of the biosensor.

Three (3) biosensors, A, B and C, were used in our experiments. Biosensors A and B were constructed from the same Pt film whereas biosensor C was constructed from a new Pt film.

Silanization (step 1) of the chemical reactions for immobilizing anti-SEB antibodies on the biosensor, primarily involves the surface hydroxyl groups, —OH extending from the uncovered portions 15 of insulator layer 11 between Pt islands 14. Because Pt can also form surface —O and —OH groups, it is also silanized to some degree. The thiol group, —SH, on the silane reacts specifically with the maleimide region of the heterofunctional crosslinker GMBS. The unreacted end of GMBS consists of the succinimide residue which reacts with an amine group, —NH$_2$, of anti-SEB. The anti-SEB is covalently bound to the modified substrate surface with a peptide bond, most likely at one of the ends of the IgG protein where steric effects would be the smallest. Antibodies covalently immobilized onto silica surfaces by similar methods do not lose activity and, thus, are also effective.

Figure 2:
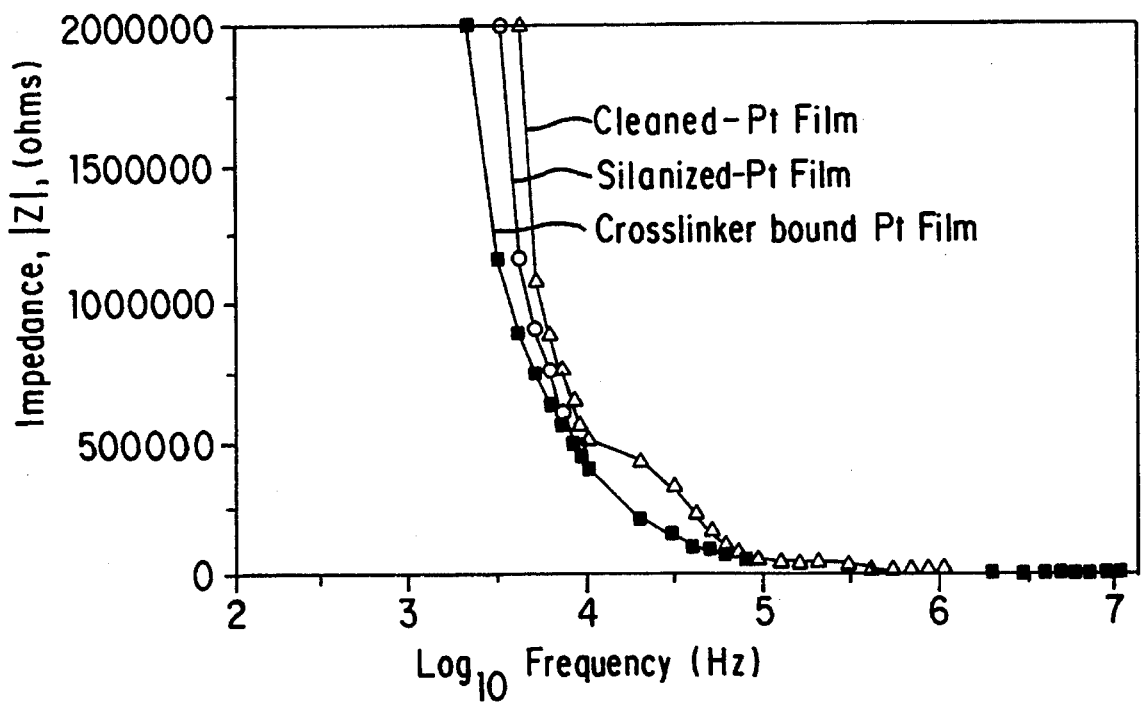
FIG. 2 shows an impedance spectra, impedance as a function of the a.c. frequency of the applied voltage, of a biosensor having a dry Pt ultra-thin film.
Figure 3:
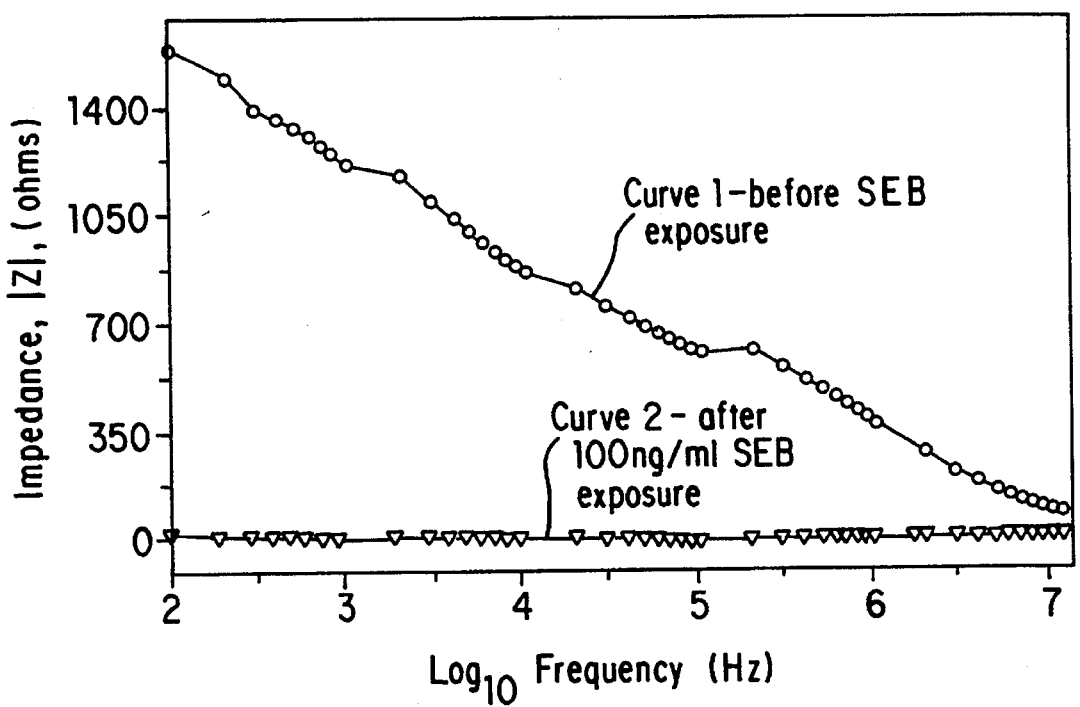
FIG. 3 shows the impedance spectra for a biosensor in accordance with one embodiment of this invention.

FIG. 2 shows the impedance spectra, impedance (|Z|) as a function of the a.c. frequency, obtained for a dry Pt film in three (3) different stages during the antibody immobilization process, cleaned-Pt film, silanized-Pt film, and crosslinker bound Pt film. As can be seen, no major changes in the film impedance occur during the antibody immobilization process. The impedance of the Pt film was about 2 Mohms at low frequencies and decreased as the frequency increased. Such a relationship would be expected where the primary mechanism of conduction is through the silicon structure. When anti-SEB was immobilized, the biosensor A was kept moist with PBS. The impedance spectrum of the film with the immobilized anti-SEB in PBS is shown in FIG. 3 (curve 1). The impedance was in the 2 kohm range and very different from the dry impedance spectra (curve 2). This suggests that the mechanism of electrical conductance between neighboring Pt islands 14 is dominated by the ionic conductivity of the hydrated and buffered protein layer. However, the impedance spectrum taken after about one hour in 100 ng/ml SEB-containing PBS solution changed significantly from that of the PBS solution (curve 2). The biosensor impedance at 100 Hz dropped to 25 ohms, a 98% drop from the 1.6 kohm obtained in the PBS before exposure to SEB. This demonstrates that the biosensor of this invention is capable of differentiating between PBS and PBS-containing SEB. The impedance decrease is attributed not only to the specific binding and non-specific adsorption of SEB to the biosensor anti-SEB layer, but also to differences in dielectric and conductivity properties of the two solutions. The largest impedance drop occurred at 100 Hz, and this frequency was chosen for time dependent impedance measurements.

When the SEB-exposed sensor, apparently saturated with 100 ng/ml SEB, is washed with PBS and placed in fresh PBS, the impedance increases from 25 to 220 ohms. This shift is attributable to changes in both the conductivity of the solution and the loss of physically absorbed SEB present in the bound anti-SEB layer, that is "nonspecific binding". SEB physically absorbed onto the surface is likely washed off in PBS. The residual non-reversible impedance change is attributed to the specific binding of SEB and anti-SEB. This behavior can be confirmed by observing reversible changes in impedance following the exposure of the SEB-saturated sensor to 25, 50 and 100 ng/ml SEB solutions in separate experiments. Sensing of the specific binding reaction is achieved by observing irreversible changes in impedance caused by the formation of strongly bound antigen-antibody complex in the region of the Pt film. These irreversible changes in the impedance, an 86% drop from the 1.6 kohms of the anti-SEB alone, are the result of saturation of the specific binding sites of the immobilized anti-SEB layer of the biosensor (biosensor A) with SEB.

The island structure of the ultra-thin Pt film layer is an important feature of the biosensor of this invention. The impedance of the Pt contains both resistance and capacitive components and is a little above 2 Mohms when dry at low frequencies. However, the impedance of the film is extremely sensitive to small changes in the electric properties of the material between the islands, especially within a 25–50 Angstrom high space immediately above and within the Pt film. As previously stated, the areas between the islands are filled with immobilized anti-SEB anti-bodies. Thus, the film can be considered to be a collection of tiny electrolytic cells connected in series and parallel over the film area. The binding of an SEB molecule to an anti-SEB molecule redistributes significant charge in the region where the anti-SEB molecule is covalently bound which, in turn, decreases the observed impedance of the Pt film (increases the conductivity). Of course, the size, shape and material used in the film can be optimized for a specific range of detection and measurement (sensitivity) and for specific (size, shape, reactivity) biomolecules being detected.

Figure 4:
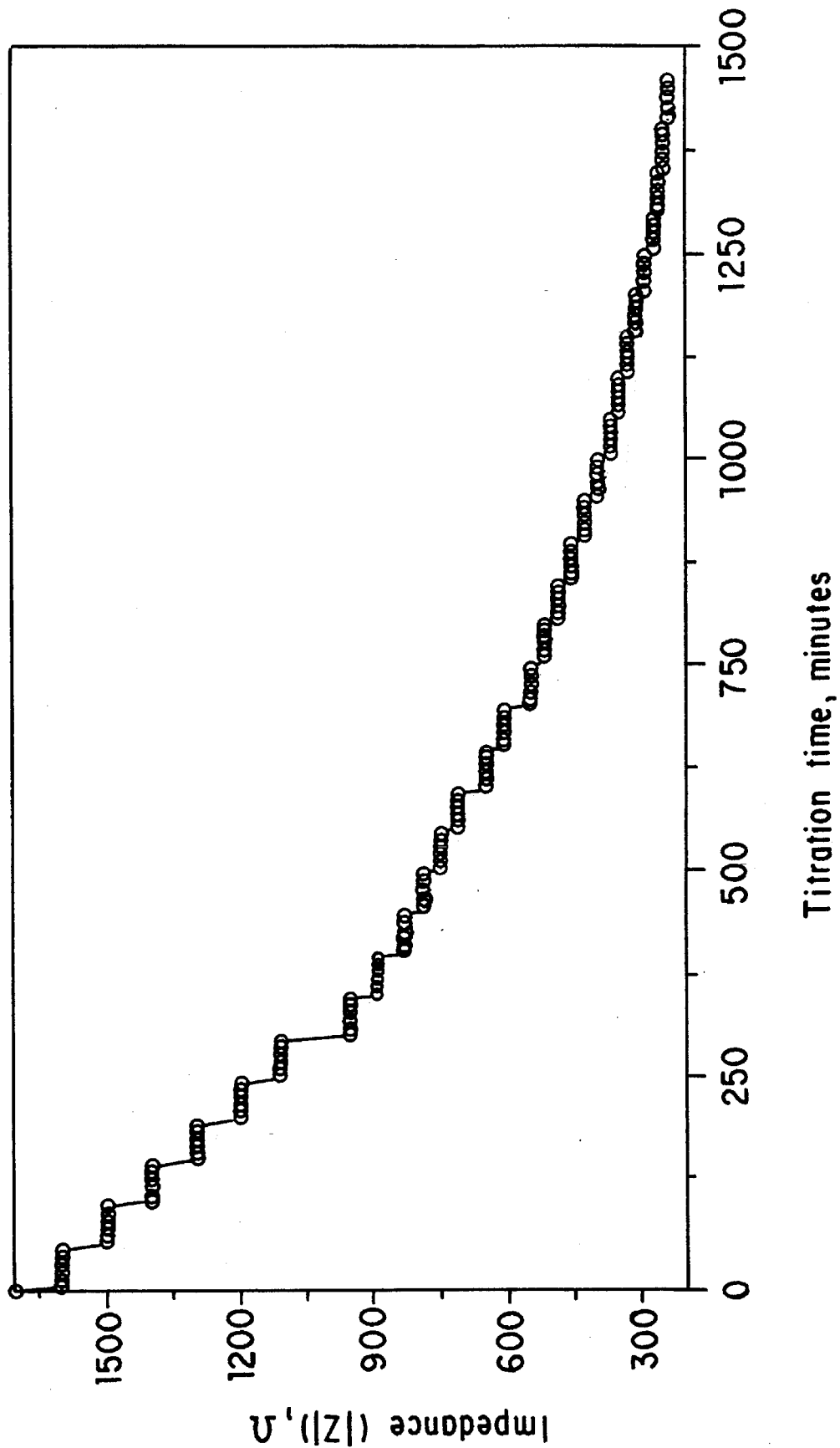
FIG. 4 shows a plot of impedance versus time for the titration of an anti-SEB layer of a second biosensor in accordance with one embodiment of this invention.

To achieve a more detailed picture of the specific antigen-antibody binding reaction, the Pt film was acid-cleaned and a fresh surface layer of anti-SEB was immobilized. A newly prepared biosensor, biosensor B, was titrated with SEB under controlled conditions. The impedance profile recorded during the cleaning and anti-SEB reimmobilization process was similar to that of the preparation of biosensor A. Biosensor B was placed in 5 ml of PBS and the reaction with SEB was followed continuously by observing the impedance at 100 Hz as SEB was added stepwise in 20 µl aliquots of a 100 ng/ml SEB solution. After each addition, the antigen-antibody reaction was allowed to reach a steady state, approximately 20 minutes, and the impedance was recorded after washing the biosensor with PBS. To determine whether the observed impedance changes were the result of specific antigen-antibody interaction, as opposed to non-specific protein interaction, the biosensor was also exposed to 100 ng/ml κ-casein at each step. κ-casein is a major protein component of milk, a food system in which the detection of Staphylococcus toxins is important. The impedance of the sensor was recorded in the κ-casein, the sensor was washed with PBS, the impedance was recorded in fresh PBS, and the sensor then placed back in the SEB solution. These impedance measurements plotted as a function of titration time produced a ladder-type curve as shown in FIG. 4. The film impedance decreased from an initial value of 1.6 kohms after each SEB addition, but did not change during rinsing with PBS or exposure to κ-casein. The irreversible change in impedance after the first SEB addition (SEB at 0.398 ng/ml) was approximately 100 ohms. The sensor was near saturation with SEB when the cumulatively added SEB concentration reached 10.7 ng/ml after 30 additions over nearly over 30 hours. The increasing time axis in FIG. 4 also represents the number of SEB additions and cumulatively increasing SEB concentration in PBS.

Figure 5:
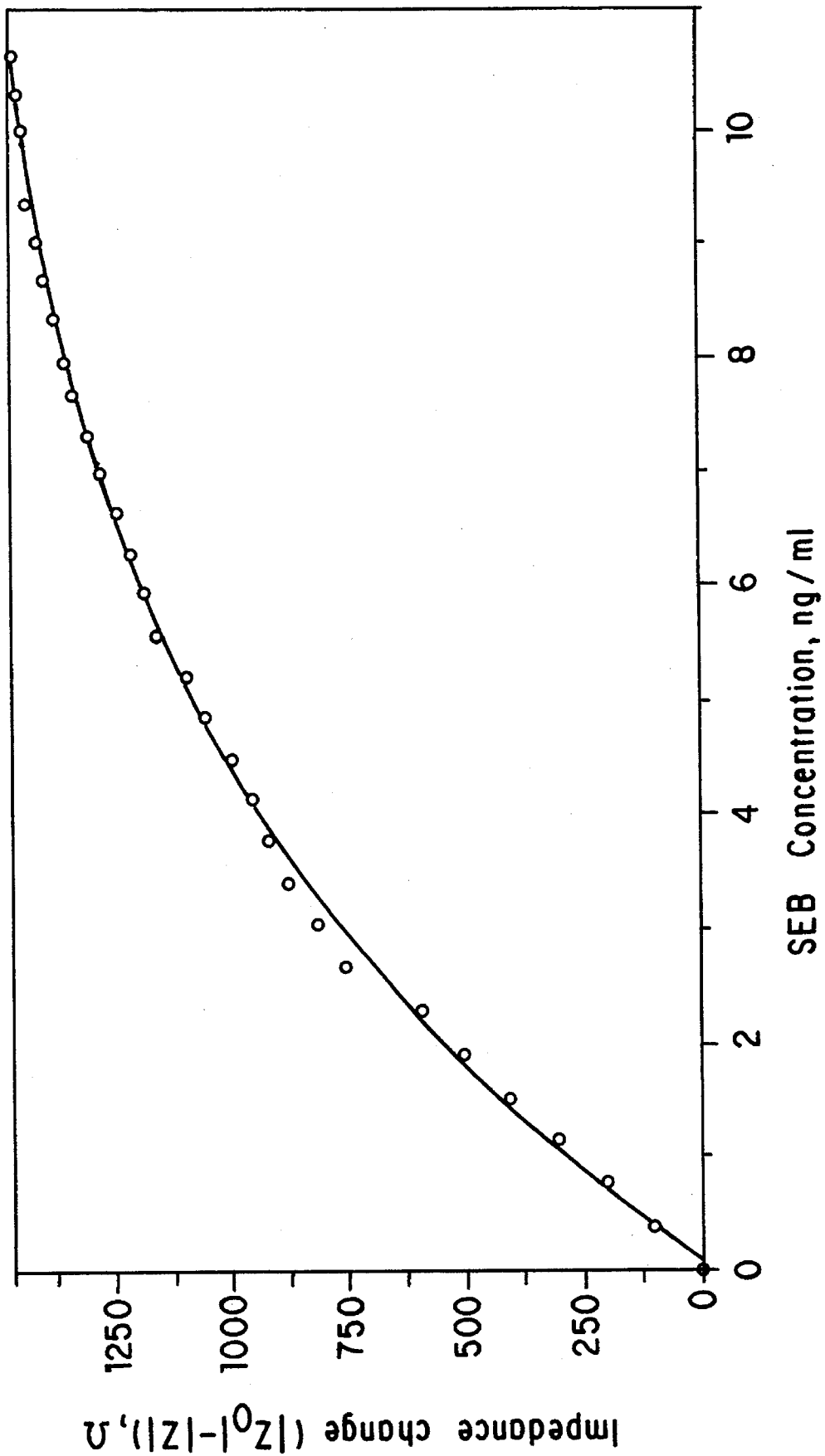
FIG. 5 is a plot of impedance change versus SEB concentration for the titration of an anti-SEB layer of a biosensor in accordance with one embodiment of this invention.

FIG. 5 is a plot of |$Z_o$|–|Z| versus the total SEB added and can be extracted from the titration curve in FIG. 4. |$Z_o$| is the initial impedance before exposure to SEB. The shape of this curve is consistent with a process where an equilibrium of specific antigen-antibody binding is involved. As the titration progressed, the surface concentration of immobilized but uncomplexed anti-SEB decreased. As a result, the extent of the complex formation should decrease to maintain the equilibrium. This may be one reason for the decrease of the size of each impedance step during the titration. The equilibrium process may also be effected by steric hindrance. The antigen-antibody complex formed in early additions may hinder access in later additions.

Figure 6:
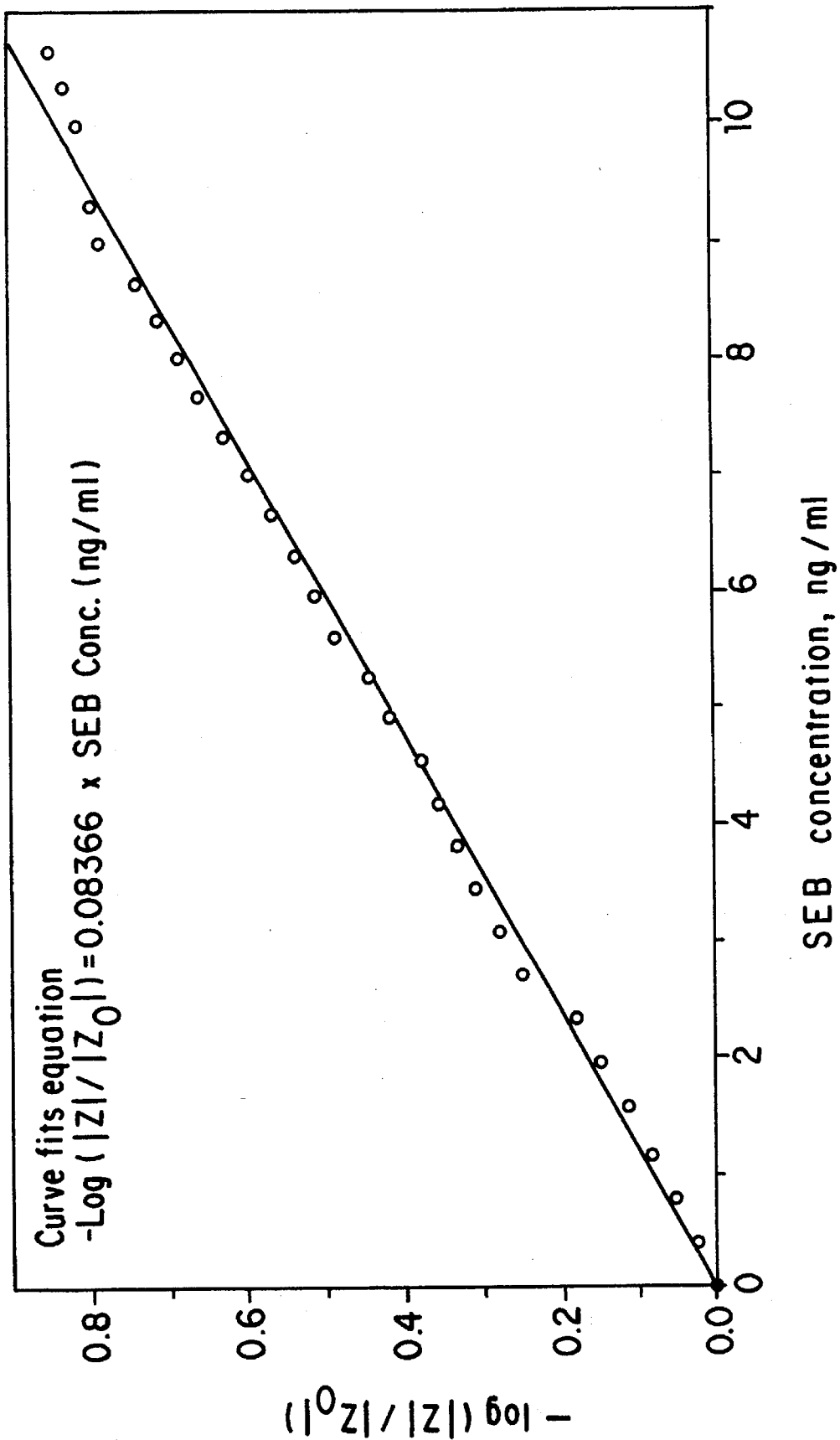
FIG. 6 is a plot of log ($|Z|/|Z_0|$) versus SEB concentration for the titration of the anti-SEB layer of a biosensor in accordance with one embodiment of this invention.
Figure 7:
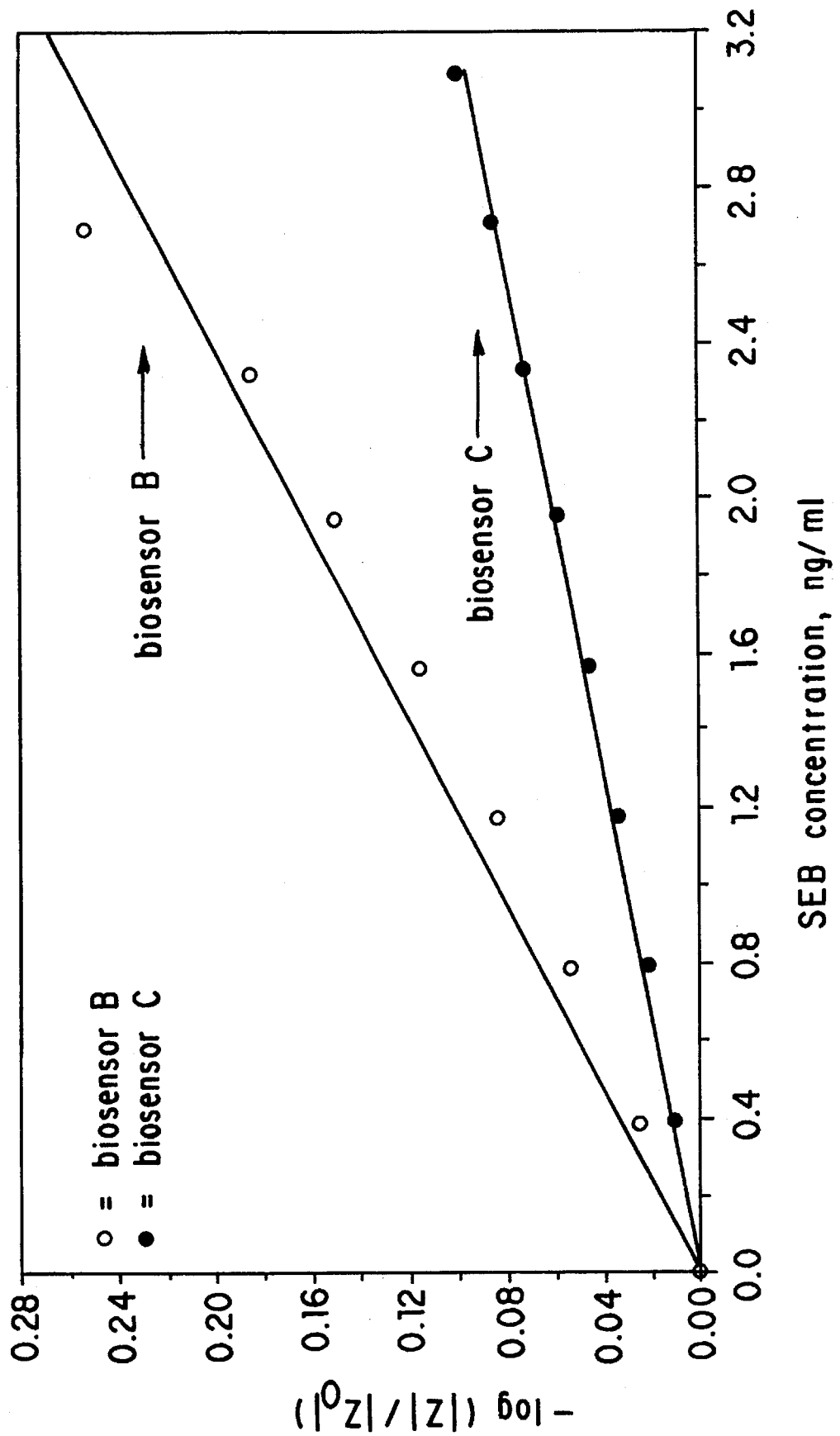
FIG. 7 is a plot of log ($|Z|/|Z_0|$ versus SEB concentration for the titration of the anti-SEB layers of two (2) biosensors utilizing two (2) different metal films in accordance with two (2) embodiments of this invention.

FIG. 6 shows a plot of $-\log(|Z|/|Z_o|)$ versus total SEB concentration, the relationship of which corresponds to the following equation with a correlation coefficient of 0.9964:

$$-\log |Z|/|Z_o| = \underline{n}[SEB]$$

where $|Z_o|$ and $|Z|$ are the impedances of the biosensor before SEB addition and at any SEB concentration during the titration, respectively. The value of $\underline{n}$ for biosensor B is 0.0836 ng$^{-1}$ ml when SEB concentration is given in ng/ml. Another biosensor in accordance with this invention, biosensor C, was prepared using a second Pt film in the same way as biosensor B. After similar experiments, a value of $\underline{n} = 0.026$ ng$^{-1}$ ml was derived for biosensor C. FIG. 7 shows that the response of biosensors B and C was similar and logarithmic, but the sensitivities differed.

Biosensors in accordance with this invention, particularly those specific for food-born microbial toxins, are intended for use in complex environments containing a large number of proteins. As previously stated, the quantitative relationship between the concentration of target antigen and the change of impedance shown by biosensor B was not effected by exposure to the milk protein κ-casein at each step in the titration. To extend this test of potential interference, biosensor C was partially saturated with SEB, the SEB being at 2.72 ng/ml, giving an impedance drop to 330 ohms from an initial value of 400 ohms, and exposed 100 ng/ml each of three (3) milk proteins (FIG. 8). Western blotting and ELISA assays show that the anti-SEB had no detectable affinity for any of these proteins. The partially saturated sensor was washed in PBS, exposed to κ-casein, washed, exposed to α-casein, washed, exposed to α-lactalbumin, and returned to PBS. The impedance was recorded throughout. No impedance change was observed when the sensor was exposed to either casein solution, or in subsequent PBS washes. However, when the sensor was placed in an α-lactalbumin, the impedance dropped to 320 ohms. This impedance drop was completely reversible when the sensor was washed in PBS. α-lactalbumin is smaller than α-casein and κ-casein and SEB, and may be able to diffuse into the anti-SEB layer on the sensor surface, effecting the measured impedance. Because it is not specifically bound by the antibodies, the α-lactalbumin was removed during subsequent PBS washes.

The use of chemically immobilized antibodies and a discontinuous Pt film on a silicon substrate make the biosensor of this invention unique. The discontinuous Pt film was composed of Pt islands with separations in the same range as the antibodies. The antibodies provided the biological specificity, and measurement of impedance decreases were used to relate the extent of antigen-antibody binding to the electrical properties of the biosensor film. Using the biosensor of this invention, it is possible to measure the microbial toxin SEB, using anti-SEB antibodies, at concentrations as low as 0.398 ng/ml, which is well below the minimal levels considered to be a public health concern (1–10 ng/ml). The lower detection limit has not yet been characterized and may be even lower.

As previously stated, the biosensor of this invention described hereinabove is particularly suited to the detection of anti-SEB antibodies-SEB antigen binding reactions. In accordance with this embodiment, the discontinuous ultra-thin metal film layer is Pt. However, metals suitable for use in biosensors in accordance with this invention may also be palladium, gold, iridium, rhodium, osmium and mixtures thereof. Also, the size and shape of the film and geometry of electrode spacing can be chosen to obtain the optimum performance for a given bioreceptor-antigen pair. The film may vary from virtually zero thickness to a solid material.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A biosensor comprising:

a substrate material;

at least one covalently bound antibody immobilized on said substrate material; and impedance detection means for measuring an impedance of said biosensor.

2. A biosensor in accordance with claim 1, wherein said substrate material is a material capable of being processed by at least one semiconductor device process.

3. A biosensor in accordance with claim 2, wherein said substrate material is a planar semiconductor device.

4. A biosensor in accordance with claim 3, wherein said substrate material comprises an insulator layer passivated on a silicon chip.

5. A biosensor in accordance with claim 4, wherein said insulator layer is silicon dioxide.

6. A biosensor in accordance with claim 4 further comprising a discontinuous ultra-thin metal film layer deposited on said insulator layer.

7. A biosensor in accordance with claim 6, wherein said discontinuous ultra-thin metal film layer comprises a plurality of distributed islands of metal with an uncovered portion of said insulator layer disposed between neighboring said islands.

8. A biosensor in accordance with claim 7, wherein a size of said uncovered portion of said insulator layer between said neighboring islands corresponds to a size range of said at least one covalently bound antibody.

9. A biosensor in accordance with claim 6, wherein said metal is selected from the group consisting of platinum, palladium, gold, iridium, rhodium, osmium and mixtures thereof.

10. A biosensor in accordance with claim 6, wherein said at least one covalently bound antibody is disposed on said discontinuous ultra-thin metal film layer.

11. A biosensor in accordance with claim 6, wherein said impedance detection means comprises two metal contact electrodes disposed on said discontinuous ultra-thin metal film layer.

12. A biosensor in accordance with claim 4, wherein said impedance detection means comprises two metal contact electrodes disposed on said insulator at a distance from one another.

13. A biosensor in accordance with claim 12, wherein said at least one covalently bound antibody is disposed on at least one of said insulator layer and said two metal contact electrodes.

14. A process for producing a biosensor for measuring antigen-antibody binding reactions comprising:

thermally growing an insulator layer on a silicon chip substrate;

depositing a discontinuous ultra-thin metal film layer on said insulator;

securing two metal contact-electrodes at a distance from each other on said discontinuous ultra-thin metal film layer; and covalently immobilizing at least one antibody bioactive layer on said discontinuous ultra-thin metal layer.

15. A process in accordance with claim 14, wherein said insulator layer is a silicon dioxide layer thermally grown in a dry oxygen atmosphere at a temperature in the range of about 900° C. to 1300° C.

16. A process in accordance with claim 14, wherein said metal is selected from the group consisting of platinum, palladium, gold, iridium, rhodium, osmium and mixtures thereof.

17. A process in accordance with claim 16, wherein said metal is platinum.

18. A process in accordance with claim 14, wherein said discontinuous ultra-thin metal film layer comprises a plurality of distributed islands of metal with an uncovered portion of said insulator layer disposed between neighboring said islands.

19. A process in accordance with claim 14, wherein said discontinuous ultra-thin metal film layer is electrically deposited on said insulator layer by one of sputtering and evaporation.

20. A process in accordance with claim 14, wherein said at least one antibody is anti-SEB.

21. A process in accordance with claim 20, wherein said anti-SEB layer is immobilized by silanization of the surface of said discontinuous ultra-thin metal film layer followed by reaction of said silanized said discontinuous ultra-thin metal film layer with a crosslinking agent and then said anti-SEB.

22. A process in accordance with claim 21, wherein said anti-SEB is covalently bound to said silanized discontinuous ultra-thin metal film layer by a chemical bond.

23. A process in accordance with claim 22, wherein said anti-SEB is covalently bound to said silanized discontinuous ultra-thin metal film layer by a peptide bond.

24. A process in accordance with claim 14, wherein said two metal contact-electrodes are connected to a header through gold-plated copper wires with silver epoxy and cured at about 150° C. for about 30 minutes.

25. A process for measuring antigen-antibody binding reactions comprising:

contacting a material comprising a chosen antigen with a biosensor comprising a substrate material, at least one covalently bound antibody corresponding to said chosen antigen immobilized on said substrate material, and impedance detection means for measuring an impedance of said biosensor; and measuring the impedance between two metal contact-electrodes of said biosensor.

* * * * *